United States Patent [19]

Stanker et al.

[11] Patent Number: 5,552,295
[45] Date of Patent: Sep. 3, 1996

[54] MONOCLONAL ANTIBODIES TO BOVINE HAPTOGLOBIN AND METHODS FOR DETECTING SERUM HAPTOGLOBIN LEVELS

[75] Inventors: Larry H. Stanker; Cynthia L. Sheffield; John R. DeLoach, all of College Station, Tex.

[73] Assignee: The United States of America as represented by the Secretary of Agriculture, Washington, D.C.

[21] Appl. No.: 205,669

[22] Filed: Mar. 2, 1994

[51] Int. Cl.$^6$ .................. G01N 33/53; G01N 33/543; C07K 16/18; C12N 5/20
[52] U.S. Cl. .................. 435/7.92; 435/240.27; 435/975; 436/518; 436/548; 530/388.1
[58] Field of Search .................. 436/518, 548; 530/392, 385, 388.1; 435/975, 240.27, 7.92, 975

[56] References Cited

PUBLICATIONS

Busby and Travis, 1978, Comp. Biochem Phys. vol. 60B pp. 389–396 "Structure and Evolution of Artiodactyla Haptoglobins".
Nakamura et al, Enzyme Immuroassays: Heterogeneous and Homogeneous system: in Handbook of Experimental Immunology. 1986 Blackwell Scientific pub. vol. 1, pp. 27.1–27.2.
"Immunogenicity and Antigen Structure in: Fundamental Immunology" Paul. ed. 1989 Raven Press, NY. pp. 177–178.
Katnik et al, 1989, Hybridoma V 8 No. 5 pp. 551–560. "Monoclonal Antibodies Against Human Haptoglobin".
Eckersall and Connor, 1990 comp. Biochem. Physiol. vol. 96B No 2 pp. 309–314. "Plasma Haptoglobin in cattle . . . ".
Campbell, "Monoclonal Antibody and Immunosensor Technology in: Laboratory techniques . . . " 1991, Elsevier Science Pub. NY, vol. 23, p. 45.
Katnik et al., 1993, Archivum Immunological and Therapial Experimentalis vol. 41 pp. 105–109. "Quantitation of Human Heptoglobin by Elisa System . . . ".

*Primary Examiner*—Toni R. Scheiner
*Assistant Examiner*—Patricia A. Duffy
*Attorney, Agent, or Firm*—M. Howard Silverstein; Randall E. Deck; John D. Fado

[57] ABSTRACT

Hybridoma cell lines have been generated which produce and secrete monoclonal antibodies which selectively bind bovine haptoglobin, either in its native state or bound to hemoglobin and/or albumin. These hybridomas may be obtained by using as an immunization agent or immunogen, bovine haptoglobin that has been complexed to hemoglobin and optionally albumin. Total bovine haptoglobin, including both native and bound to hemoglobin and/or albumin, present in biological samples may be detected and quantified by contacting the sample with the antibodies to form a bovine haptoglobin/antibody immunocomplex when the bovine haptoglobin is present, which immunocomplex may then be detected. The monoclonal antibodies may also be incorporated into kits for the detection and quantification of bovine haptoglobin.

18 Claims, 6 Drawing Sheets

FIG 1

Lane 1 - Control Plasma Retentate (CPR)
Lane 2 - Test Plasma Retentate (TPR)

FIG 2

Lane 1 - Human Hb - Stained
Lane 2 - Human Hp type 2-2 - Stained
Lane 3 - TPR - Stained
Lane 4 - CPR - Stained
Lane 5 - Human Hb - Immunoprobed
Lane 6 - Human Hp type 2-2 - Immunoprobed
Lane 7 - TPR - Immunoprobed
Lane 8 - CPR - Immunoprobed

Lane 1 - CPR - Stained
Lane 2 - TPR - Stained
Lane 3 - TPR - Immunoprobed
Lane 4 - CPR - Immunoprobed
Lane 5 - Bovine Hb - Immunoprobed
Lane 6 - TPR - Immunoprobed
Lane 7 - TPR & Bovine Hb - Immunoprobed

FIG 5

MONOCLONAL ANTIBODIES TO BOVINE HAPTOGLOBIN AND METHODS FOR DETECTING SERUM HAPTOGLOBIN LEVELS

BACKGROUND OF THE INVENTION

1. Field of the Invention

This invention relates to hybridoma cell lines and monoclonal antibodies produced therefrom which may be used to detect haptoglobin.

2. Description of the Prior Art

Haptoglobin is a macromolecular glycoprotein which is the major acute phase reactant in cattle and other ruminants [Bremner, 1964, Aust. J. Exp. Biol. Med. Sci., 42:643–656; Goodger, 1970, Clin. Chim. Acta., 29:429–435; Blakeslee and Stone, 1971, Vox Sang., 21:175–182; Spooner and Miller, 1971, Vet. Rec., 12:2–4; Putnam, 1975, Haptoglobin, In: The Plasma Proteins, Structure, Function, and Genetic Control, 11, Putnam (ed.), Academic Press, New York, pp. 1–50; Blackshaw, 1979, NZ Vet. J., 27:103–105; Eckersall and Conner, 1990, Comp. Biochem. Physiol., 96B:309–314; and Morimatsu et al., 1991, J. Biol. Chem., 266:11833–11837].

Biochemical studies have shown that bovine haptoglobin is composed of two chains, an alpha-chain and a beta-chain. The reported molecular weights of the chains has varied among investigators, with the alpha-chain having been described as 16 and 23 KDa, and the beta-chain having been described as 40 and 35 KDa [Morimatsu et al., ibid, Eckersall and Conner, ibid]. Two alpha-chains and two beta-chains are linked by a disulfide bond, forming the basic tetrameric subunit of the compound. In biological material such as blood, haptoglobin binds to hemoglobin, forming a stable complex therewith [Putnam, ibid; Morimatsu et al., ibid]. Eckersall and Conner (ibid) have also reported that haptoglobin is associated with albumin in bovine plasma. The basic tetrameric subunit and albumin associate into polymers of varying molecular weight. Eckersall and Conner have reported molecular weights of 670 KDa and Morimatsu et al. have reported variable molecular weights up to 2000 KDa.

As an acute phase reactant, haptoglobin serum levels become greatly elevated immediately following injury or infection. Clinically, less than 5% of healthy cattle have measurable levels [10 mg % hemoglobin binding capacity (HbBC)] of haptoglobin in their serum (Bremner; Goodger; Blakeslee and Stone; Spooner and Miller; Blackshaw; and Eckersall and Conner, all ibid). However, a rapid increase in the serum haptoglobin level occurs following infection, inflammation or trauma, with serum levels exceeding 100 mg % HbBC of haptoglobin within 3 to 4 days following trauma (Spooner and Miller, ibid). Haptoglobin therefore represents a nonspecific, highly sensitive indicator of disease or tissue damage in cattle [Liberg, 1977, Acta Vet. Scand., 18:335–348; Dinarello, 1984, Induction of Acute Phase Reactants by Interleukin-1, IN: Advances in Inflammation Research, 8, Weissman (ed.), Raven Press, New York, pp. 203–225; Conner et al., 1986, Res. Vet. Sci., 41:126–128; and Eckersall and Conner, 1988, Vet. Res. Commun., 12:169–178].

Considerable research has dealt with illuminating the conditions that stimulate the production of haptoglobin and the in vivo time course of haptoglobin production [Blakeslee and Stone; Spooner and Miller; Liberg; Blackshaw; Dinarello; Conner et al. 1986; and Eckersall and Conner 1988, all ibid; and Conner et al., 1986 Prot. Biol. Fluids, 34:509–512; Conner et al., 1988, Res. Vet. Sci., 44:82–88; Conner et al., 1989, Res. Vet. Sci., 47:203–207; Erskine and Ridell, 1990, The Acute Phase Response During Experimental *Escherichia coli* Mastitis, In: The International Symposium on Bovine Mastitis, Sep. 13–16, 1990, Indianapolis, Ind., pp. 60–63; and Makimura and Usui, 1990, Jpn. J. Vet. Sci., 52(6):1245–1250]. Additional studies have focused on the purification and biochemical characterization of haptoglobin [Owen et al., 1960, J. Clin. Pathol., 13:163–164; Bremner, ibid; Goodger 1970, ibid; Goodger, 1972, Aust. J. Exp. Biol. Med. Sci., 50:11–20; Javid and Liang, 1973, J. Lab. Clin. Med., 82:991–1002; Spooner, 1973, Res. Vet. Sci., 4:90–96; Makimura and Suzuki, 1982, Jpn. J. Vet. Sci., 44:15–21; Osada, 1985, Acta Biochim. Pol., 32:225–233; Eckersall and Conner 1990, ibid; Morimatsu et al., ibid; Skinner et al., 1991, Vet. Rec., 128:147–149; and Yoshino et al., 1992, Am. J. Vet. Res., 53(6):951–956].

There exists a need for an indicator of preclinical illness in cattle to reduce the number of carcasses condemned after slaughter. However, the use of serum haptoglobin levels as this diagnostic tool has been hampered by the lack of a simple, rapid, and sensitive assay for determining haptoglobin concentrations. The current method used to quantify haptoglobin is a colorimetric procedure based upon the difference in peroxidase activity between free hemoglobin and the hemoglobin-haptoglobin complex (Owen et al.; and Makimura and Suzuki, both ibid). Unfortunately, this is a cumbersome assay, and the accuracy of the method is dependent upon the quality of the sample, particularly the collection of plasma that is free of hemoglobin contamination.

SUMMARY OF THE INVENTION

We have now discovered hybridoma cell lines which produce and secrete monoclonal antibodies which selectively bind haptoglobin, either in its native state or bound to hemoglobin and/or albumin. We have unexpectedly found that these hybridomas may be obtained by using as an immunization agent or immunogen, haptoglobin that has been complexed to hemoglobin and optionally albumin. Total haptoglobin, including both native and bound to hemoglobin and/or albumin, present in biological samples may be detected and quantified by contacting the sample with the antibodies to form a haptoglobin/antibody immunocomplex when the haptoglobin is present, which immunocomplex may then be detected. The monoclonal antibodies may also be incorporated into kits for the detection and quantification of haptoglobin.

It is an object of this invention to provide hybridoma cell lines that produce and secrete high affinity monoclonal antibodies which selectively bind haptoglobin, and which are effective for detecting free haptoglobin and haptoglobin conjugated to hemoglobin and/or albumin.

Another object of this invention is to provide immunoassay methods for the measurement of haptoglobin in biological samples as an indicator of preclinical illness in animals, particularly bovine.

A further object is to provide kits useful for the assay of bovine haptoglobin which include the monoclonal antibodies described herein.

Other objects and advantages of this invention will become readily apparent from the ensuing description.

DETAILED DESCRIPTION OF THE INVENTION

In accordance with this invention we have created hybridoma cell lines that produce monoclonal antibodies which selectively bind haptoglobin not only in its native state but also haptoglobin bound to hemoglobin and/or albumin. Without being limited thereto, the invention is particularly suited to the production of monoclonal antibodies binding to haptoglobin of ruminants such as goats, sheep, deer and especially bovine. The antibodies may be used to rapidly and accurately detect and quantify haptoglobin, providing an indicator of preclinical illness in animals such as cattle and reducing the number of carcasses condemned after slaughter.

Serum samples are often contaminated with hemoglobin that binds to haptoglobin, interfering with traditional analytical methods. Although the development of specific antibodies would be desirable for the detection of haptoglobin in biological samples, here again the presence hemoglobin may interfere and lead to inaccurate results. For example, the antigen-antibody binding of many monoclonal antibodies generated to pure haptoglobin may be sterically inhibited or prevented by the presence of hemoglobin contaminants bound to the haptoglobin molecule. Depending upon the degree of hemoglobin contamination and its inhibition of antibody binding, this could lead to significant errors or false negative results. We have discovered that this problem may be overcome by using haptoglobin which is complexed to hemoglobin as an immunization agent for the preparation of hybridomas. The monoclonal antibodies produced by these hybridomas bind to haptoglobin at non-hemoglobin binding sites on the molecule, and consequently bind to both free haptoglobin and haptoglobin that is complexed to hemoglobin in the sample. The antibodies therefore provide an accurate tool for the measurement of total haptoglobin in biological samples that is free from interference by hemoglobin contaminants.

In a particularly preferred embodiment, the immunization agent also includes albumin conjugated to the haptoglobin together with hemoglobin. Although not essential, inclusion of albumin is highly desirable to generate hybridoma cell lines producing monoclonal antibodies that bind to native haptoglobin as well as haptoglobin bound to hemoglobin and/or albumin. As noted hereinabove, albumin has also been reported bind with haptoglobin in biological samples such as blood. By use of a haptoglobin-hemoglobin-albumin complex as the immunization agent, monoclonal antibodies that bind to haptoglobin at non-hemoglobin and non-albumin binding sites may be produced. Not only would the binding of these monoclonal antibodies be free of interference by hemoglobin contaminants, they would also be free from interference by albumin as well.

Preparation of the hybridomas may be accomplished using conventional techniques such as described by Kohler and Milstein [Nature, 256:495–497 (1975)], Koprowski et al. [U.S. Pat. No. 4,196,265], Wands [U.S. Pat. No. 4,271,145], or Stanker et al. [U.S. patent application Ser. No. 08/081,591, filed Jun. 23, 1993], the contents of each of which are incorporated by reference herein. Generally, the process of preparation comprises the steps of immunizing an animal with the antigen of interest, recovering splenocytes or lymphocytes from the animal, fusing the splenocytes or lymphocytes with continuously replicating myeloma cells to produce hybrid cells, and screening the resultant hybrid cells for the production of antibodies to the antigen.

The method of preparing the hybridomas comprises the following steps:

Immunogen. The immunizing agent is constructed by complexing haptoglobin with hemoglobin and optionally albumin. In a preferred embodiment, the immunogen is derived from the plasma of subject traumatized animals, particularly bovine. The manner of traumatizing the animal is not critical, and a variety of treatments effective for eliciting haptoglobin production which are known in the art may be used herein. Without being limited thereto, preferred traumatizing treatments include humane exposure to non-lethal levels of inflammatory agents or noxious chemicals, particularly turpentine. Following treatment, plasma from the subject animals may be recovered, usually about 3 to 4 days after treatment. Rather than isolating the haptoglobin from the plasma in pure form, ideally, the haptoglobin is only partially purified, so as to maintain it in association with hemoglobin and albumin from the original sample. Without wishing to be limited to theory, this partial purification would also allow the haptoglobin to be maintained in association with any other as yet currently unknown binding proteins. To ensure complex formation, hemoglobin may be optionally added to the plasma sample. The manner of recovering the haptoglobin-hemoglobin complex from the plasma is not critical, and a variety of techniques may be used including, but not limited to, dialysis or diafiltration to remove low molecular weight components (below 300 KDa). The resultant partially purified haptoglobin-hemoglobin complex may be used directly as an immunogen.

In an alternative embodiment, the immunogen may be readily prepared from pure haptoglobin. Conditions for the complex formation are not critical; haptoglobin may be contacted with hemoglobin and preferably albumin in any suitable solvent, such as physiologically buffered saline or water, with spontaneous complex formation.

Immunization. To generate antibody-producing splenocytes or lymphocytes, an immunizing preparation comprising the haptoglobin-hemoglobin complex is injected into an immunologically competent animal. The preparation may also contain other proteins, although partially purified compositions of the conjugate in a pharmaceutically acceptable carrier are preferred.

Without being limited thereto, rats and particularly mice are preferred animals for immunization because of ease of handling. Preparation of hybridomas using splenocytes from these animals fused to a variety of myeloma cell lines have been reported by many investigators.

Inoculations of the animal can be by various routes. A series of three inoculations, generally at two week intervals, with a composition of the complex in isotonic saline with RIBI adjuvant (Immunochem Research, Inc., Hamilton, Mont.) elicits good antibody response, and is preferred. The skilled practitioner will recognize that other routes of administration, immunization schedules, and carriers or adjuvants may be used.

Hybridization. Splenocytes or lymphocytes recovered from the immunized animal are fused with continuously replicating tumor cells, such as myeloma or lymphoma cells, cultured, and hybridoma cells selected using techniques conventional in the art. Many continuously replicating tumor cell lines are available which may be used as fusion partners with the splenocytes. Without being limited thereto, preferred myeloma cells include P3-NS1-K653, and particularly SP2/O.

Fusion and culture of the cells can be performed using conventional techniques. In accordance with one well known effective procedure, the splenocytes and myeloma cells are fused by exposure to polyethylene glycol. Hybrid cells are selected by culture in hypoxanthine-aminopterin-thymidine (HAT) medium, whereby unfused myeloma cells are killed by HAT and splenocytes die out, leaving only the hybrid cells. The resultant hybridomas are then grown in HAT or other suitable culture medium and assayed for antibody production.

Screening. Samples of the supernatant culture fluid from the hybridomas are screened for antibodies to haptoglobin. While the supernatants may be screened using a plurality of techniques such as RIA, FIA and ELISA, in accordance with the preferred embodiment, a modification of the direct-binding ELISA (db-ELISA) is employed. Generally, solid substrates, such as beads or the wells of a microtiter plate, which are coated with haptoglobin or haptoglobin-hemoglobin complex, are used to bind anti-haptoglobin antibody in the supernatants, and bound antibody is then detected. Detection of bound antibody may be accomplished by addition of enzyme-labeled anti-immunoglobulin antibodies followed by enzyme substrate. Horse radish peroxidase and its substrate, 2,2'-azinobis-3-ethylbenthiazolinesulfonic acid (ABTS) are preferred enzyme/substrate labels. However, it is understood that other enzyme/substrate labels or non-enzyme labels such as radiolabels or chromophores may also be used. The skilled practitioner will recognize that in the event that this screening is conducted using substrates coated with complexed haptoglobin (haptoglobin complexed with hemoglobin and/or albumin), the antibodies should also be screened against a control, such as hemoglobin and/or albumin, or control plasma from a non-traumatized animal. This additional screen is necessary to ensure that only those antibodies are selected which specifically bind haptoglobin, but not hemoglobin, albumin or other serum proteins.

Cloning. Cloning of hybridomas which are positive for desired antibody production can be carried out as soon as they are detected by any method known in the art. Hybridomas having a positive response in the ELISA screen are preferably expanded and subcloned one or more times by limiting dilution to assure monoclonality.

The supernatant culture fluid from the cloned hybridomas may also be screened to select for those producing antibodies having a high affinity for haptoglobin. Affinity may be measured using a variety of well known techniques, such as ELISA, RIA or equilibrium dialysis using labelled haptoglobin.

Once hybridomas producing and secreting the desired anti-haptoglobin antibodies are identified, large quantities of the antibody may be produced in tissue culture using well-known techniques. Alternatively, antibody may be produced within host animals, such as by ascites formation in syngenic mice.

The monoclonal antibodies produced in accordance with this invention possess high affinity for haptoglobin, allowing the rapid determination of this acute phase reactant. The antibodies my be used in a variety of conventional immmosorbent assays to detect and/or quantify haptoglobin in unknown biological samples. Furthermore, immunoassay of haptoglobin with the antibodies provides much greater sensitivity to haptoglobin, and allows the detection of haptoglobin elevation in animals such as bovine much earlier following infection or trauma, than conventional biochemical methods.

Suitable assay procedures include but are not limited to RIA or ELISA, although competitive inhibition ELISA or a direct-binding ELISA similar to that used to screen the hybridomas is preferred. In the competitive inhibition ELISA, a sample to be analyzed is incubated with the monoclonal antibody for haptoglobin and a solid substrate coated with haptoglobin. After incubation, the solid phase is drained and washed, and bound antibody on the substrate is detected and percent inhibition calculated. The concentration of haptoglobin in the sample may then be determined by reference to a standard curve. A standard curve relating the percent inhibition (amount of bound antibody) to haptoglobin concentration my be constructed from assays using known levels of haptoglobin.

In another alternative embodiment, haptoglobin may be determined by a competition ELISA such as described in Brandon et al. (U.S. Pat. No. 5,053,327, the contents of which are incorporated by reference herein) using the monoclonal antibody of the invention attached to a solid support. For example, the anti-haptoglobin antibody may be immobilized on a solid support such as a bead or microtiter well. The unknown sample to be analyzed (or analytical standards of haptoglobin) are then added with enzyme or radiolabeled haptoglobin, and the amount of labeled haptoglobin bound to the antibody is measured, using a substrate when the label is an enzyme. The amount of haptoglobin in the sample is inversely proportional to the amount of bound labeled haptoglobin. In yet another alternative, the monoclonal antibody may be attached to a solid support for use in conventional double-antibody sandwich ELISA procedures.

With any of the above-described assay formats, the monoclonal antibodies of the invention may be incorporated into kits, alone or preferably together with any other necessary reagents. A preferred kit for use herein comprises a first container including the monoclonal antibody, a second container including detection means effective for detecting bound antibody, and a solid phase support having haptoglobin attached thereto.

Determination of haptoglobin in a variety of biological samples may be conducted using the above-described assays. Without being limited thereto, the assays are particularly advantageous for determining haptoglobin levels in serum, plasma and whole blood.

In another application, the monoclonal antibodies may be incorporated into sensors such as solid phase electronic devices for detection of haptoglobin in sample materials.

The following examples are intended only to further illustrate the invention and are not intended to limit the scope of the invention which is defined by the claims.

EXAMPLE 1

Immunogen Production

Haptoglobin Induction. The immunogen preparation used for the development of the monoclonal antibodies was derived from the plasma of turpentine-treated cattle. Four purebred Hereford heifers (average body weight (BW)= 132 kg) were housed individually in indoor stalls, and fed a diet of grass hay and a commercial range cube supplement. The heifers were acclimated for 2 weeks to their diet and surroundings. The treatment and control groups each contained two heifers. All heifers were anesthetized by an intravenous injection of xylazine at a rate of 0.11 m/kg BW. When the animal reached a light surgical plane of anesthesia, an injection site located 6" caudal to the shoulder and 3" below the midline measuring approximately 2"×6" was shaved and cleaned by 3 washes with Betadine, followed by a final wipe down with isopropyl alcohol. Each treatment animal then received three 5 mL subcutaneous injections of commercial grade turpentine approximately 2" apart. The control animal received three 5 mL subcutaneous injections of sterile normal saline approximately 2" apart. All animals were revived by an intravenous injection of Tolazoline (300 mg/animal). Once alert, the heifers were returned to their stalls and maintained as before. None of the animals evidenced any signs of discomfort or required any specialized care. All of the procedures involving the research animals were conducted as outlined in protocol #91008 which was approved by the USDA, ARS Animal Care and Use Committee in College Station, Tex. On days 2 to 5, post-treatment, 500 mL of blood/animal were collected via jugular venipuncture into sterile bottles containing 100 mL of anticoagulant citrate dextrose solution (Sonofi Animal Health, Inc.). The erythrocytes were separated from the plasma by centrifugation at 1000× g for 30 min. The plasma was recovered and stored at −70° C.

Haptoglobin Processing. Plasma from the treated animals was thawed and delipidated by the addition of Seroclear (Cal Biochem, Inc., San Diego, Calif.) according to the manufacturer's instructions. In some instances, bovine hemoglobin was added to the delipidated, plasma and this material was diafiltered using an Amicon Stirred Cell Chamber (Amicon, Inc., Danvers, Mass.) fitted with a 300 KDa molecular weight cutoff membrane. The retentate was washed 3 to 4 times with 100 mL of phosphate buffered 0.9% saline (PBS; pH 7.4). After the final rinse and filtration, the sample was resuspended in 10 mL of PBS, representing approximately a 10-fold concentration of the starting material. This retentate was aliquoted and stored at −70° C. until needed and is referred to as the test plasma retentate (TPR). Plasma from the control animal was processed similarly and is referred to as the control plasma retentate (CPR).

Standard Curve Generation. The 4-day post-treatment test plasma (TP) was diluted with control plasma as follows: 60% TP, 36% TP, 22% TP, 13% TP, 8% TP, and 5% TP. The haptoglobin level was determined as the mg % HbBC (hemoglobin binding capacity) using the differential peroxidase method of Owen et al. (1960, J. Clin. Path., 13:163 –164), the contents of which are incorporated by reference herein. These samples were then used in an ELISA as described in Example 2 to generate a standard curve. The plasma samples collected at 4-days post-treatment from turpentine treated test cows were found to have a haptoglobin level of 104 mg % HbBC by the differential peroxidase method. The plasma samples collected 4-days post-treatment from the control cows were found to have no detectable level of haptoglobin.

SDS-Polyacrylamide Gel Electrophoresis (SDS-PAGE). Both TPR and CPR were analyzed by SDS-PAGE using 4–15% precast TRIS-HCl gradient gels (BioRad, Inc., Richmond, Calif.). Samples (50 µL) were loaded and electrophoresed at 50 milliamps constant current for 1 hour (Laemmli, 1970). The gels were stained with Coomassie R-250 Brilliant Blue (0.2% Coomassie R-250 Brilliant Blue (w/v), 25% isopropyl alcohol, 10% acetic acid) for 1 hour, then destained (in 25% isopropyl alcohol, 10% acetic acid) until a colorless background was obtained.

Figure 1:
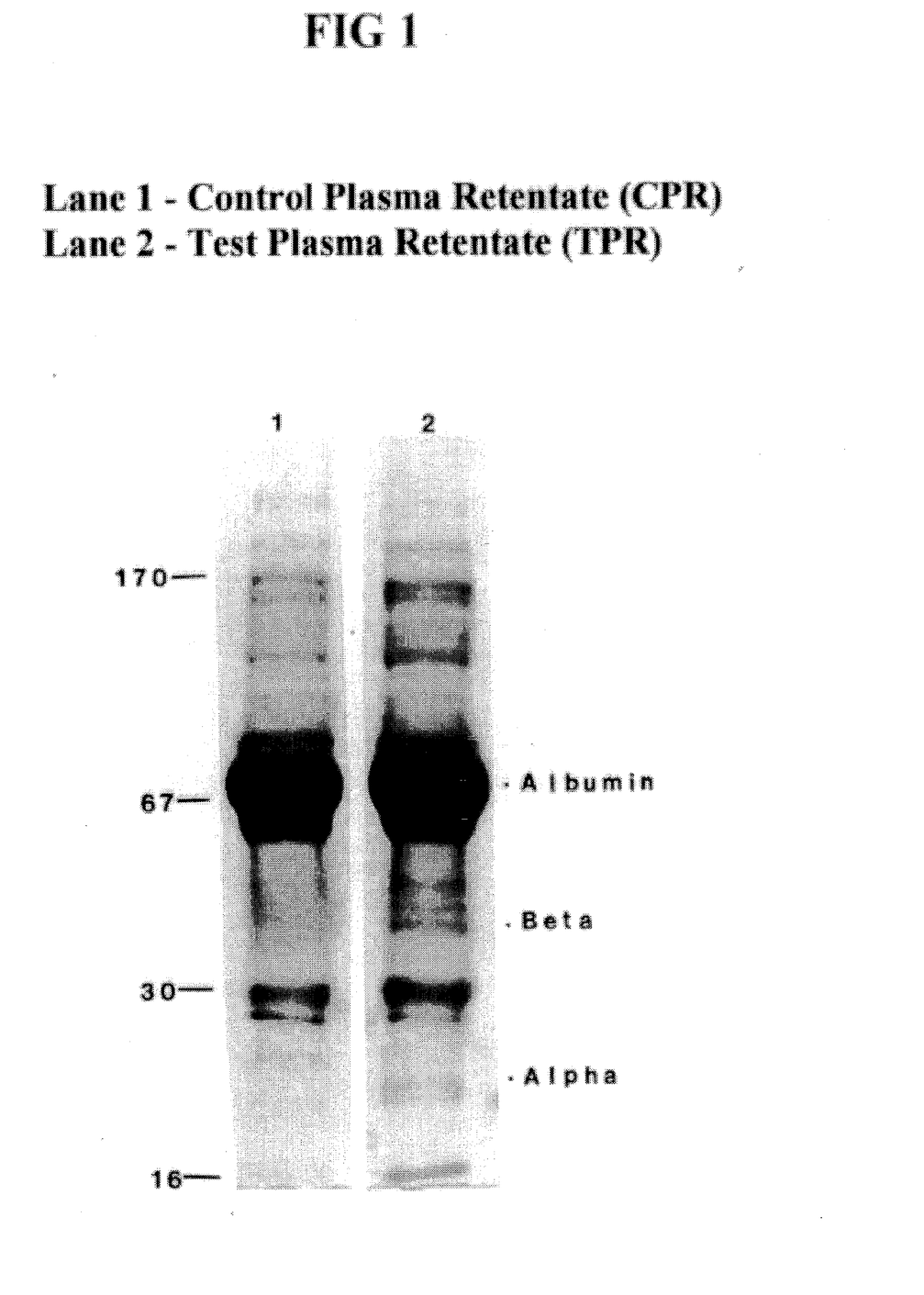
FIG. 1 shows an SDS-PAGE gel of test and control plasma retentates.

SDS-PAGE analysis of the TPR revealed two bands not present in the CPR; the beta-subunit of haptoglobin with a molecular weight of 38.3 KDa and the alpha-subunit of haptoglobin with a molecular weight 22.5 KDa (arrows) (FIG. 1, lanes 1 and 2). Both the TPR and CPR contained numerous other proteins, primarily albmuin.

Thin Layer Agarose. Thin layer agarose gel electrophoresis was performed on TPR, TPR with bovine hemoglobin added, and CPR using precast gels (Titan Gel Serum Protein System, Helena Laboratories Inc., Beaumont, Tex.). Samples (3 µl) were loaded and electrophoresed at 120 volts for 15 min. The gels were fixed in 100% methanol for 5 min., dried at 70° C. for 15 min., then stained and destained as described above.

Cellulose Acetate. Cellulose acetate electrophoresis was also conducted on the plasma retentates. The cellulose acetate plates were soaked for 10 to 15 min. in Titan Gel High Resolution Protein Buffer (Helena Laboratories Inc., Beaumont, Tex.) prior to sample application. A 10 g % solution of stabilized human hemoglobin (Helena Laboratories Inc., Beaumont, Tex.) was mixed in a 1:20 ratio with the plasma retentate samples and allowed to stand at room temperature for 5 min. Samples were applied to the cellulose acetate plate using the Super-Z applicator (Helena Laboratories Inc., Beaumont, Tex.) and electrophoresed at 180 volts for 20 min. After electrophoresis, the plates were fixed and stained according to the manufacturer's instructions (Helena Laboratories Inc., Beaumont, Tex.).

Figure 2:
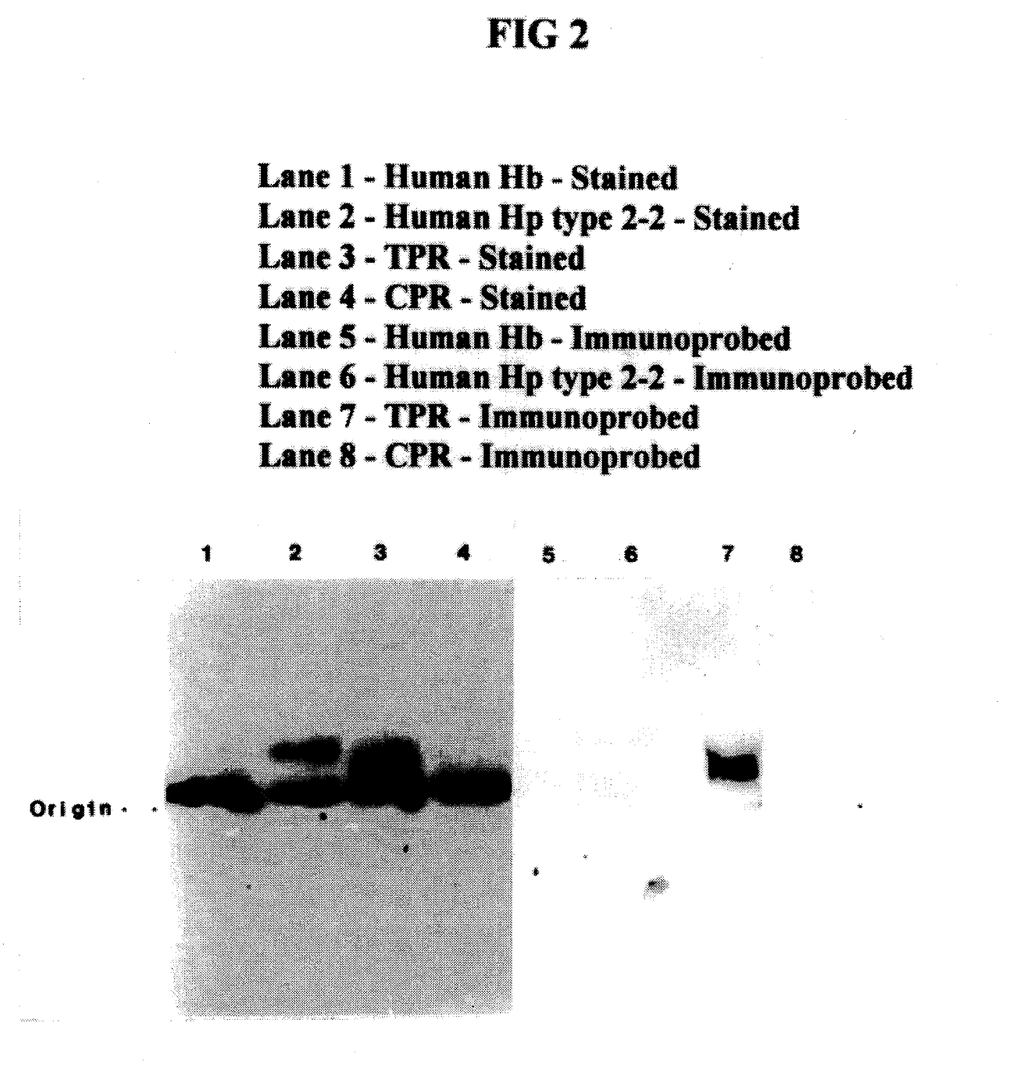
FIG. 2 shows a cellulose acetate electrophoresis gel of test and control plasma retentates.

Results from our analysis of TPR and CPR for haptoglobin using the Helena Cellulose Acetate system are shown in FIG. 2. The single band migration pattern of hemoglobin is shown in lane 1. A mixture of human hemoglobin and human haptoglobin type 2–2 was electrophoresed and showed the characteristic two band pattern (lane 2). The lower band is excess hemoglobin while the upper band is the hemoglobin-haptoglobin complex. Electrophoresis of a mixture of TPR and human hemoglobin (lane 3) also showed 2 bands, the lower hemoglobin band and an upper hemoglobin-haptoglobin complex. In contrast, identical analysis of CPR (lane 4) displayed only a single hemoglobin band. The cellulose acetate gels were stained with 0-dianisidine, which is a stain specific for hemoglobin.

The Helena cellulose acetate electrophoresis method used is a clinical method for the evaluation of human haptoglobin (Valeri et al., 1965). A similar cellulose acetate electrophoresis method was used by Goodger (1970, ibid) to detect bovine haptoglobin. The electrophoretic conditions used in the Helena cellulose acetate method were designed to give maximum separation of the human hemoglobin-haptoglobin complex, which is quite different from the bovine complex (Goodger, 1972, ibid; Eckersal et al., 1988, ibid). For this reason, the bovine hemoglobin-haptoglobin complex, though clearly present (FIG. 2, lane 3), does not give as sharp a separation as does the human complex (FIG. 2, lane 2). Nevertheless, the results of the cellulose acetate haptoglobin assay clearly demonstrated that the TPR contains a hemoglobin binding protein (FIG. 2, lane 3) that is not found in the CPR (FIG. 2, lane 4). This hemoglobin binding protein, is by definition, haptoglobin (Bremner; Spooner and Miller; Goodger, 1972; Osada; Eckersall and Conner, 1990; Makimura and Usui; and Morimatsu et al., all ibid). Thus, the results of the SDS-Page and the Helena cellulose acetate electrophoresis both confirm that the TPR, used as antigen to immunize the mice, contained bovine haptoglobin.

EXAMPLE 2

Hybridoma Production

The use of a partially purified immunogen (TPR) from Example 1 allowed the haptoglobin to be maintained in association with both albumin and hemoglobin, thus enabling the selection of monoclonal antibodies (Mabs) which can detect haptoglobin when bound to hemoglobin. However, the use of a complex antigen necessitated a differential screening procedure to ensure isolation of a haptoglobin specific Mab. These efforts yielded three haptoglobin specific Mabs and one bovine hemoglobin specific Mab.

The protein concentration of the hemoglobin containing TPR was determined using the Sigma Total Protein Colorimetric Endpoint Diagnostic kit (St. Louis, Mo.). The hemoglobin-haptoglobin TPR was combined with RIBI adjuvant (Immunochem Research, Inc., Hamilton, Mont.) to a final protein concentration of 250 µg/mL and was used to immunize BALB/c mice. The mice were given three intraperitoneal (Ip) antigen injections (100 µL/injection) at 14 day intervals. A final Ip injection was given five days prior to fusion. Ten days after the second immunization, plasma was collected from each mouse by retro-orbital bleeding. The mice were given a subcutaneous injection of a 10× diluted solution of Fentanyl Citrate-Droperidol (Innovar Vet, Pittmon-Moore, Washington Crossing, N.J.) 5 to 10 min. prior to bleeding.

The mouse with the highest serum titer for TPR, when screened against TPR and CPR in an ELISA as described hereinbelow, was selected for fusion. Hybridomas were generated by fusion to mouse myeloma cells as described by Stanker et al. (1986, J. Immunol., 136(11);4147–4180), the contents of which are incorporated by reference herein. The cell fusion product was spread over 30, 96-well plates.

Screening. Eleven to fifteen days after fusion, the hybridomas were screened for antibodies that were positive against test plasma (TPR) and negative against control plasma (CPR) using an ELISA. At fourteen days post-fusion, greater than 90% of the wells contained hybridomas.

Cells that had a positive response to the test plasma and a negative response to the control plasma were transferred to 24-well plates, expanded, and subcloned at least twice by limiting dilution to ensure their monoclonal origin. Additional screening of all clones was conducted on microtiter plates coated with TPR, CPR, and bovine hemoglobin.

ELISA. The ELISA technique described below was used for all screening and subsequent testing of animal plasma. Microtiter plates (96-well) were coated with 100 µL of antigen (TPR, CPR or bovine hemoglobin in 50 mM carbonate buffer pH 9.6) at a concentration of 100 ng total protein/well, and dried overnight at 37° C. Immediately prior to use, nonreacted sites on the plates were blocked by adding 3% nonfat dry milk (NFDM) in phosphate buffered saline pH 7.0 (PBS-7) and incubating the plate for 30 min. The blocking solution was then discarded and 100 µL/well of the anti-haptoglobin Mab, either in the form of neat cell culture media (used in preliminary screens) or a 1:1000 dilution of purified antibody stock (1.4 mg/mL in 1% NFDM PBS-7 solution)(AB), was added and the plate incubated for 1 hour at 37° C. After incubation, the anti-haptoglobin Mab was discarded and the plates washed 5 times in a 0.05% TWEEN-20/deionized water detergent wash solution (DWS) and once in deionized water. Goat anti-mouse IgG-whole molecule-peroxidase conjugate (Sigma Inc., St. Louis, Mo.), diluted 1:500 with AB was then added to the plate (100 µL/well), and the plate incubated 1 hour at 37° C. and washed as described above. Finally, 100 µL/well of substrate (0.8 mM [2,2'-azino-bis(3-ethylbenzthiazoline-6-sulfonic acid)] (ABTS), 0.001% $H_2O_2$, in a 0.1M citrate buffer pH 5.0) was added. The plate was then incubated for 45 min. at room temperature, and the O.D. at 405 nm recorded.

Figure 3A:
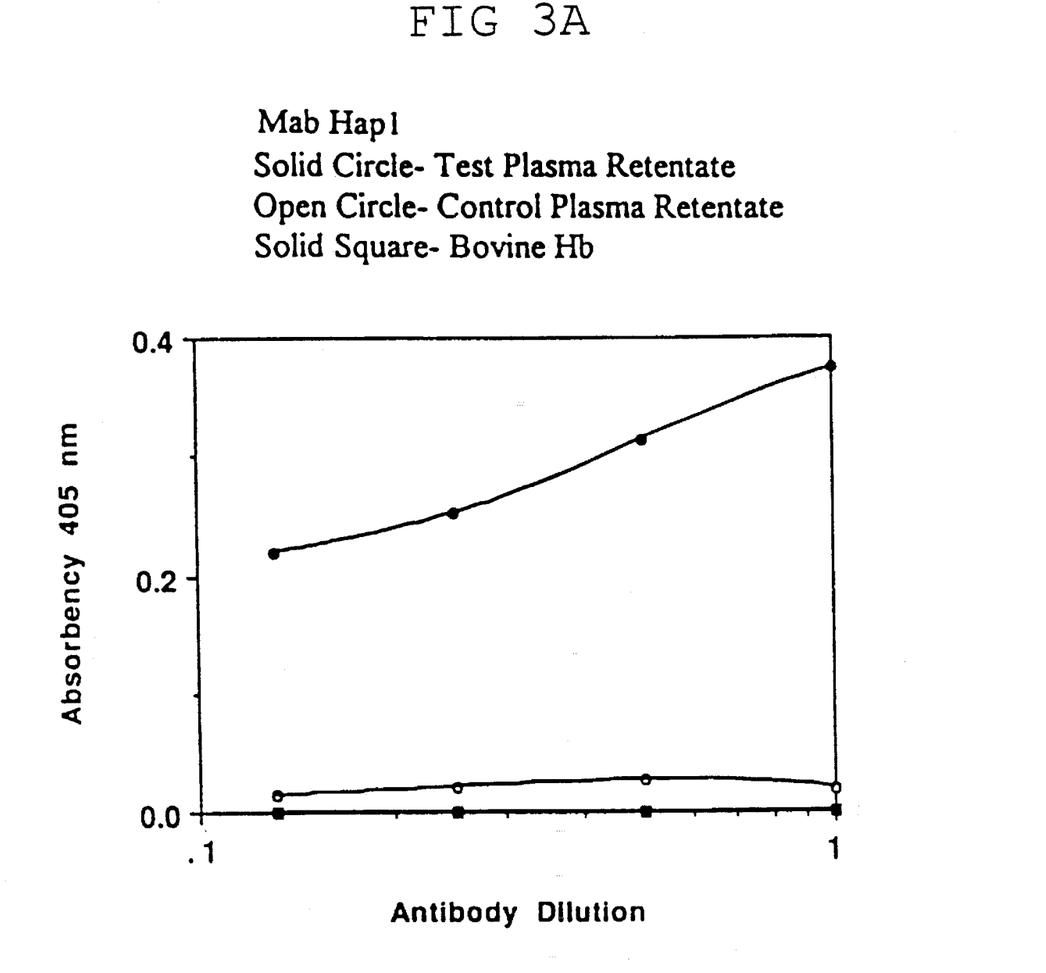
FIGS. 3A and 3B show typical ELISA results of monoclonal antibody analysis on Microtiter plates coated with test plasma retentate, control plasma retentate, and bovine hemoglobin.
Figure 3B:
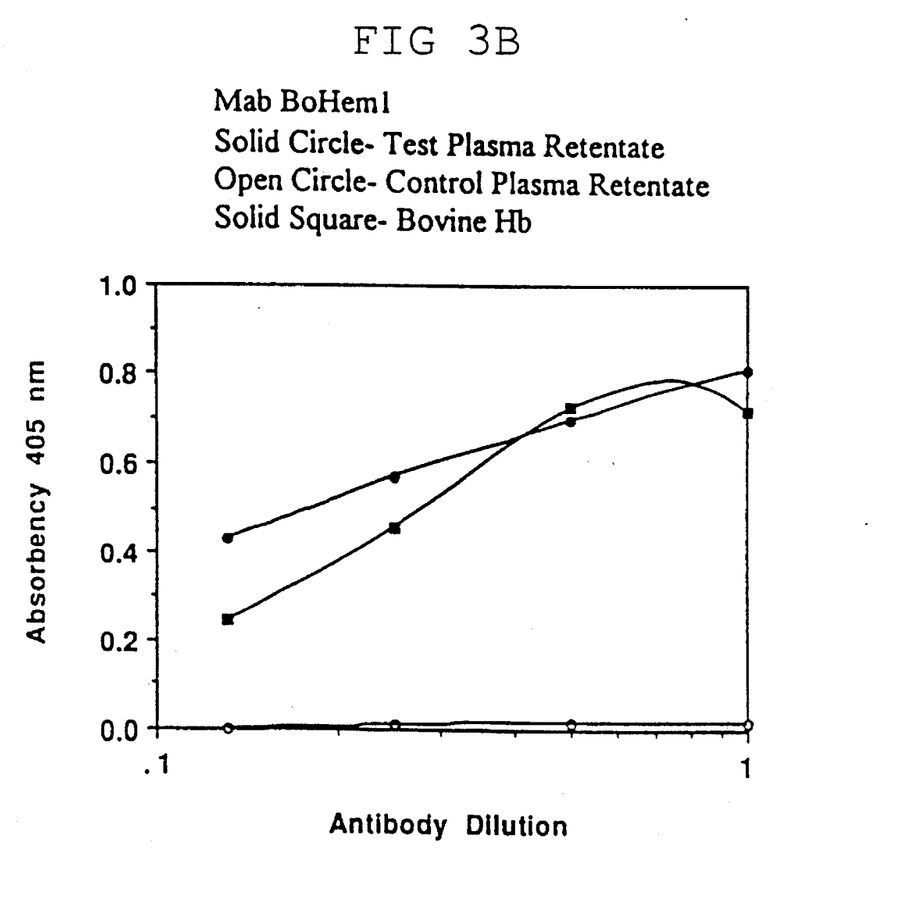

Eighty wells contained hybridomas that responded positively to the TPR and negatively to the CPR. Cells from these wells were subcloned twice by limiting dilution. Only 14 clones survived the subcloning process. Subsequent characterization of these Mabs by ELISA revealed 12 clones that bound TPR but not CPR or bovine hemoglobin (anti-haptoglobin Mabs) and 2 clones that bound both TPR and bovine hemoglobin (anti-bovine Mabs). The 3 clones (designated Hap1, Hap2, Hap3) with the highest titer to TPR, and the clone designated (BoHem1) with the highest titer to bovine hemoglobin were selected for further examination. FIGS. 3A and 3B are a typical ELISA titration showing the reactivity of Hap1 (Panel A) and BoHem1 (Panel B) on the antigens indicated. The titration curves in FIG. 3A clearly show that Hap1 bound the TPR (solid circle), but not CPR (open circle) or bovine hemoglobin (solid square). In contrast, BoHem1 (FIG. 3b) bound the TPR (solid circle) and bovine hemoglobin (solid square), but not CPR (open circle). Monoclonal antibody Hap1 was selected for assay development and immunoblotting evaluations.

Hybridoma Isotyping. The four monoclonal antibodies were isotyped according to manufacturer's recommendations, using the FisherBiotech (Fisher Scientific, Pittsburgh, Pa.) isotyping kit. All were found to be IgG1-kappa antibodies.

Immunoblotting. The antibodies were further characterized by immunoblotting using the electrophoresis gel samples prepared as in Example 1 (SDS-PAGE, Thin Layer Agarose, and Cellulose Acetate).

a. Thin Layer Agarose:

Following electrophoresis, the thin layer agarose gels (Titan Gel Serum Protein System, Helena Laboratories, Inc., Beaumont, Tex.) were dried overnight at 37° C. without fixation. Immediately prior to immunoblotting, the gels were blocked with 3% BSA PBS-7 for 30 min. The gels were then incubated (1 hour at room temperature with gentle agitation) in the following sequence of materials:

A) 8 mL of Hap1 Mab, either in the form of neat cell culture media, or a 1:1000 dilution in 0.05M Tris-HCl buffered saline pH 7.4 (TBS) of purified antibody stock (1.4 mg/mL);

B) 8 mL of biotinylated anti-mouse antibody (Sigma Inc., St. Louis, Mo.) diluted 1:1000 in TBS;

C) 8 mL of streptavidin-biotinylated-alkaline phosphatase conjugate (Sigma Inc., St. Louis, Mo.) diluted 1:1000 in TBS. The gels were washed 5 times with 8 mL of DWS after each incubation. The gels were then incubated at room temperature without agitation for no longer than 30 min. in 8 mL of color development reagent (5-bromo-4-chloro-3-indolylphosphate, BCIP; p-nitro blue tetrazolium chloride, (NBT); Sigma Inc., St. Louis, Mo.).

b. SDS-PAGE:

Proteins from 4–15% SDS gradient gels were transferred onto Immobilon-P transfer membrane (Millipore, Bedford, Mass.) in a semi-dry transfer cell (BioRad Laboratories, Hercules, Calif.). The Bjerrum and Schafer-Nielsen transfer buffer system recommended by the manufacturer (BioRad Laboratories, Hercules, Calif.) was used for all transfers. The proteins were then visualized following the same immunoblotting procedure described above.

c. Cellulose Acetate:

Cellulose acetate plates were air dried at room temperature overnight. The proteins were then visualized following the same immunoblotting procedure described above.

d. Results:

Samples identical to those electrophoresed on the cellulose acetate (FIG. 2, lanes 1–4) were probed with Mab Hap1 (FIG. 2, lanes 5–8). Hap1 labeled only a single protein (lane 7), corresponding in position to the bovine haptoglobin-hemoglobin complex seen in lane 3. No immunoprecipitation bands are observed in lane 5 (free Hemoglobin), lane 6 (human Haptoglobin 2–2), or lane 8 (CPR).

Figure 4:
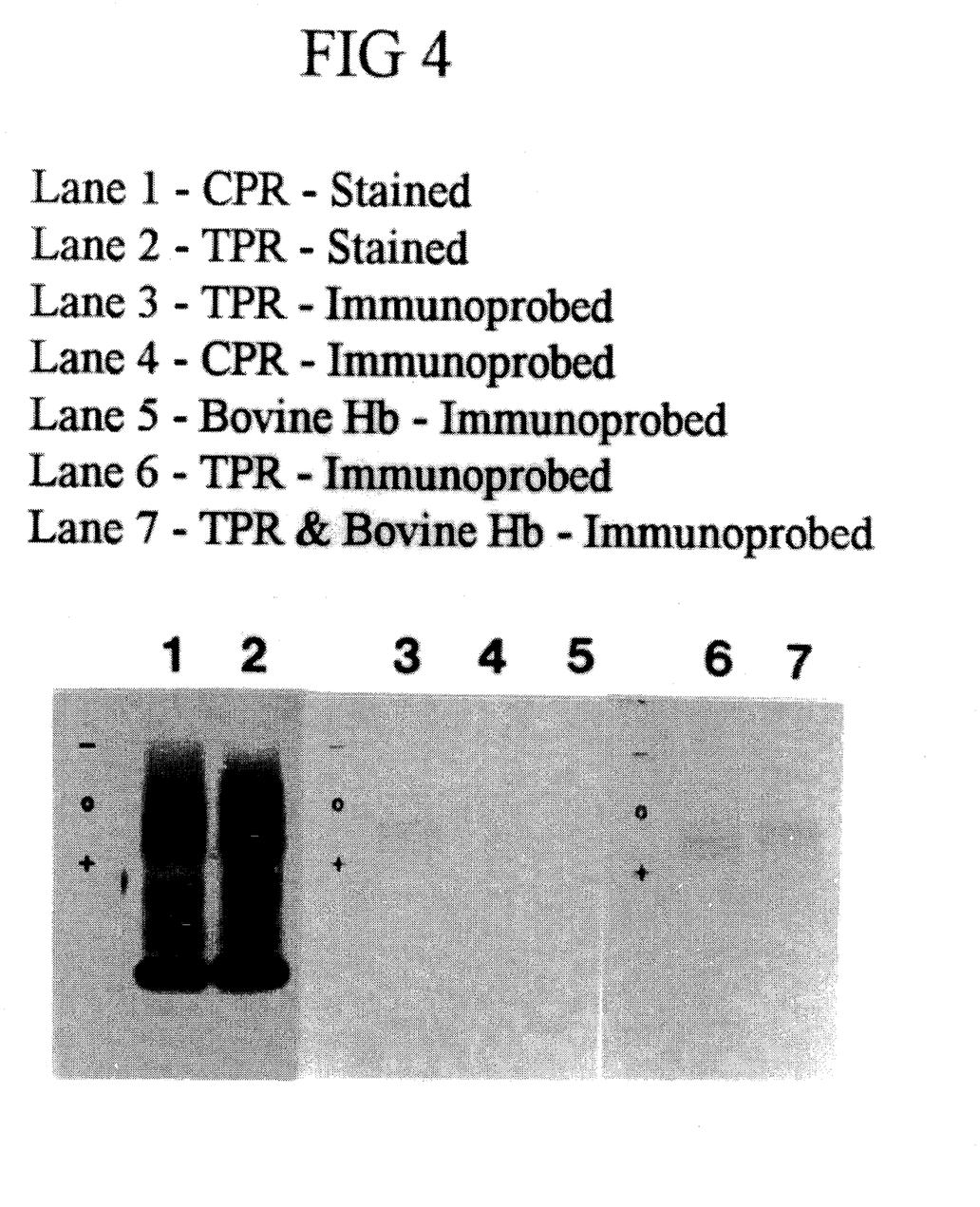
FIG. 4 shows an immunoblot of a thin layer agarose electrophoresis gel of test and control plasma retentates.

Shown in FIG. 4 is a thin layer agarose gel probed with Hap1. Numerous proteins were observed in both the CPR and TPR lanes when stained with Coomassie Brilliant Blue (FIG. 4, lanes 1–2). In contrast, when Hap1 was used as a probe, only a singly protein band was labeled when TPR was analyzed (lanes 3 and 6), and no protein bands were labeled when CPR was analyzed (lane 4) or when bovine hemoglobin was analyzed (lane 5). The location of the immunostained band (haptoglobin) in lane 3 corresponds to a region in lane 2 (TPR) that is more heavily stained with Coomassie Brilliant Blue than the corresponding region in lane 1 (CPR). The addition of free hemoglobin to the test plasma prior to electrophoresis, resulted in a shift of the immunostained band (lane 7) toward the cathode relative to the position of the immunostained TPR band (lane 6) (Compare FIG. 4, lane 6 with lane 7). Bremmer (ibid) using paper electrophoresis, reported that bovine hapteglobin migrated to a location between alpha$_2$-globulin and beta-globulin. Goodger (1970, ibid) also reported that on slab agarose electrophoresis, bovine hapteglobin migrated to the beta-globulin region. Liberg (ibid) reported a significant increase in the number of serum protein bands found in the region near alpha$_2$-globulin and beta-globulin in animals with signs of inflammation. This information supports the conclusion that the single immunoprecipitation band seen in this region of lanes 3 and 6 (TPR), but not in lane 4 (CPR), when the gel is probed with Hap1 Mab is, in fact, haptoglobin.

EXAMPLE 3

Haptoglobin Assay

As noted in Example 1, the day 0 and day 4 post-treatment plasma (TP) samples were assayed using the ELISA of Example 2 to determine bovine haptoglobin levels.

Figure 5:
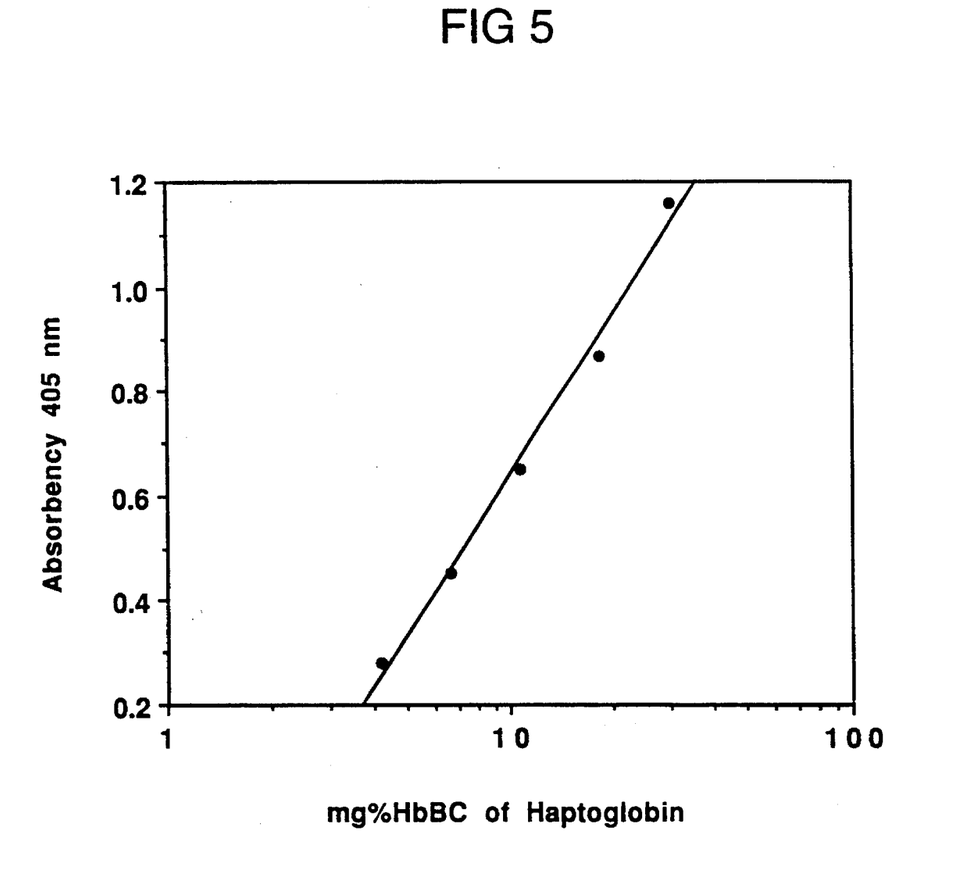
FIG. 5 shows a typical ELISA standard curve for haptoglobin. A linear regression curve fit is shown.

FIG. 5 shows a typical standard curve obtained with the ELISA. The mg % HbBC of haptoglobin in the gelatins was determined by the differential peroxidase activity method and plotted against the ELISA O.D. reading taken at 405 nm.

Shown in Table 1 are the haptoglobin levels (mg % HbBC) of plasma samples from 4 cows taken at the two timepoints, one immediately prior to treatment and the second at 4 days post-treatment. The haptoglobin levels were determined both by ELISA and by the differential peroxidase method. This data clearly shows an increase in haptoglobin levels in the test animals at day 4 post-treatment while no corresponding increase is seen in control animals. Additionally, the haptoglobin levels obtained by the ELISA method are comparable to those obtained by the differential peroxidase method.

It is understood that the foregoing detailed description is given merely by way of illustration and that modifications and variations may be made therein without departing from the spirit and scope of the invention.

TABLE 1

| | Haptoglobin Levels (mg % HbBC) | | | |
|---|---|---|---|---|
| | Day 0 | | Day 4 | |
| Animal # | ELISA[a] | Peroxidase[b] | ELISA | Peroxidase |
| Test-1[c] | 0 | 0 | 40 | 32 |
| Test 2 | 0 | 0 | 41 | 56 |
| Control-1[d] | 0 | 0 | 0 | 0 |
| Control-2 | 0 | 0 | 7 | 0 |

[a]Haptoglobin levels measured by extrapolation to standard curve shown in FIG. 5
[b]Haptoglobin levels measured by differential peroxidase method
[c]Test cows were injected with Turpentine as described in methods
[d]Control cows were injected with Normal Saline as described in methods

We claim:

1. A hybridoma cell line which produces and secretes monoclonal antibodies which specifically bind to bovine haptoglobin at non-hemoglobin binding sites.

2. The hybridoma cell line of claim 1 wherein said monoclonal antibodies specifically bind to bovine haptoglobin at non-hemoglobin and non-albumin binding sites.

3. The hybridoma cell line of claim 1 which is produced using an immunization preparation comprising a complex of bovine haptoglobin bound to hemoglobin.

4. The hybridoma cell line of claim 3 wherein said immunization preparation further comprises albmuin bound to said complex and said monoclonal antibodies specifically bind to bovine haptoglobin at non-hemoglobin and non-albumin binding sites.

5. A monoclonal antibody produced by the hybridoma cell line of claim 1.

6. A monoclonal antibody produced by the hybridoma cell line of claim 2.

7. A method for detecting or quantifying bovine haptoglobin in a biological sample comprising:
   (a) contacting said sample with the monoclonal antibody of claim 5 to form a bovine haptoglobin/antibody immunocomplex when bovine haptoglobin is present, and
   (b) detecting the presence or amount of said immunocomplex.

8. The method of claim 7 wherein said sample is selected from the group consisting of plasma, serum and whole blood.

9. The method of claim 7 wherein said contacting step comprises:
   (1) providing a solid substrate;
   (2) incubating said sample with said solid substrate to coat said substrate with any bovine haptoglobin in said sample;
   (3) rinsing said substrate;
   (4) Incubating the bovine haptoglobin coated substrate from (2) with said monoclonal antibody; and (5) rinsing said substrate;
and wherein said detecting step comprises:
  (4) detecting any monoclonal antibody bound to said substrate; and
  (5) determining the presence or amount of bovine haptoglobin in said sample.

10. A method for detecting or quantifying bovine haptoglobin in a biological sample comprising:
  (a) contacting said sample with the monoclonal antibody of claim 6 to form a bovine haptoglobin/antibody immunocomplex when bovine haptoglobin is present, and
  (b) detecting the presence or amount of said immunocomplex.

11. The method of claim 10 wherein said sample is selected from the group consisting of plasma, serum and whole blood.

12. A kit for the detection or quantification of bovine haptoglobin in a biological sample comprising a container including the monoclonal antibody of claim 5.

13. A kit for the detection or quantification of bovine haptoglobin in a biological sample comprising a container including the monoclonal antibody of claim 6.

14. A method for preparing hybridoma cell lines which produce and secrete monoclonal antibodies which specifically bind to bovine haptoglobin at non-hemoglobin binding sites comprising:
  (a) immunizing a mammal with an immunization preparation comprising a complex of bovine haptoglobin conjugated to hemoglobin;
  (b) recovering antibody-producing cells from said mammal;
  (c) fusing said antibody-producing cells with cells of a continuously replicating cell line to form hybrid cells;
  (d) screening said hybrid cells for the production of monoclonal antibodies which specifically bind to bovine haptoglobin at non-hemoglobin binding sites; and
  (e) cloning said hybrid cells from (d) producing said antibodies.

15. The method of claim 14 wherein said mammal is a mouse.

16. The method of claim 14 wherein said immunization preparation further comprises albumin conjugated to said complex.

17. The hybridoma cell lines of claim 1 which is produced by using an immunization preparation comprising a complex of bovine haptoglobin conjugated to hemoglobin, and screened for the production of monoclonal antibodies which specifically bind to bovine haptoglobin at non-hemoglobin binding sites.

18. The hybridoma cell line of claim 2 which is produced by using an immunization preparation comprising a complex of bovine haptoglobin conjugated to hemoglobin and albumin, and screened for the production of monoclonal antibodies which specifically bind to bovine haptoglobin at non-hemoglobin and non-albumin binding sites.

* * * * *